United States Patent [19]

Blackman

[11] Patent Number: 4,692,151

[45] Date of Patent: Sep. 8, 1987

[54] PARENTERAL FLUID MEDICATION RESERVOIR PUMP

[76] Inventor: Seymour N. Blackman, 1530 Palisade Ave., Fort Lee, N.J. 07024

[21] Appl. No.: 835,942

[22] Filed: Mar. 4, 1986

[51] Int. Cl.⁴ ............................................. A61M 37/00
[52] U.S. Cl. ..................................... 604/132; 604/141; 222/80; 222/212
[58] Field of Search ................. 604/81, 132, 141, 133, 604/281; 222/80, 107, 212, 213

[56] References Cited

U.S. PATENT DOCUMENTS

| | | | |
|---|---|---|---|
| 3,154,222 | 10/1964 | Heckman | 222/213 |
| 3,468,308 | 9/1969 | Bierman | 222/212 |
| 3,946,735 | 3/1976 | De Wall | 604/133 |
| 4,221,219 | 9/1980 | Tucker | 604/141 |
| 4,451,255 | 5/1984 | Bujan et al. | 604/81 |

Primary Examiner—C. Fred Rosenbaum
Assistant Examiner—J. L. Kruter
Attorney, Agent, or Firm—Kirschstein, Kirschstein, Ottinger & Israel

[57] ABSTRACT

A parenteral fluid medication pump comprises a reservoir filled with a fluid medication, and a needle insertable into a patient. The medication is continuously discharged in small doses over an extended time period through the needle into the patient. The continuous discharge is obtained by elastic walls for the reservoir which seek to return toward an original unexpanded position, or by the expansion of a compressible gas within a rigid-walled reservoir.

4 Claims, 10 Drawing Figures

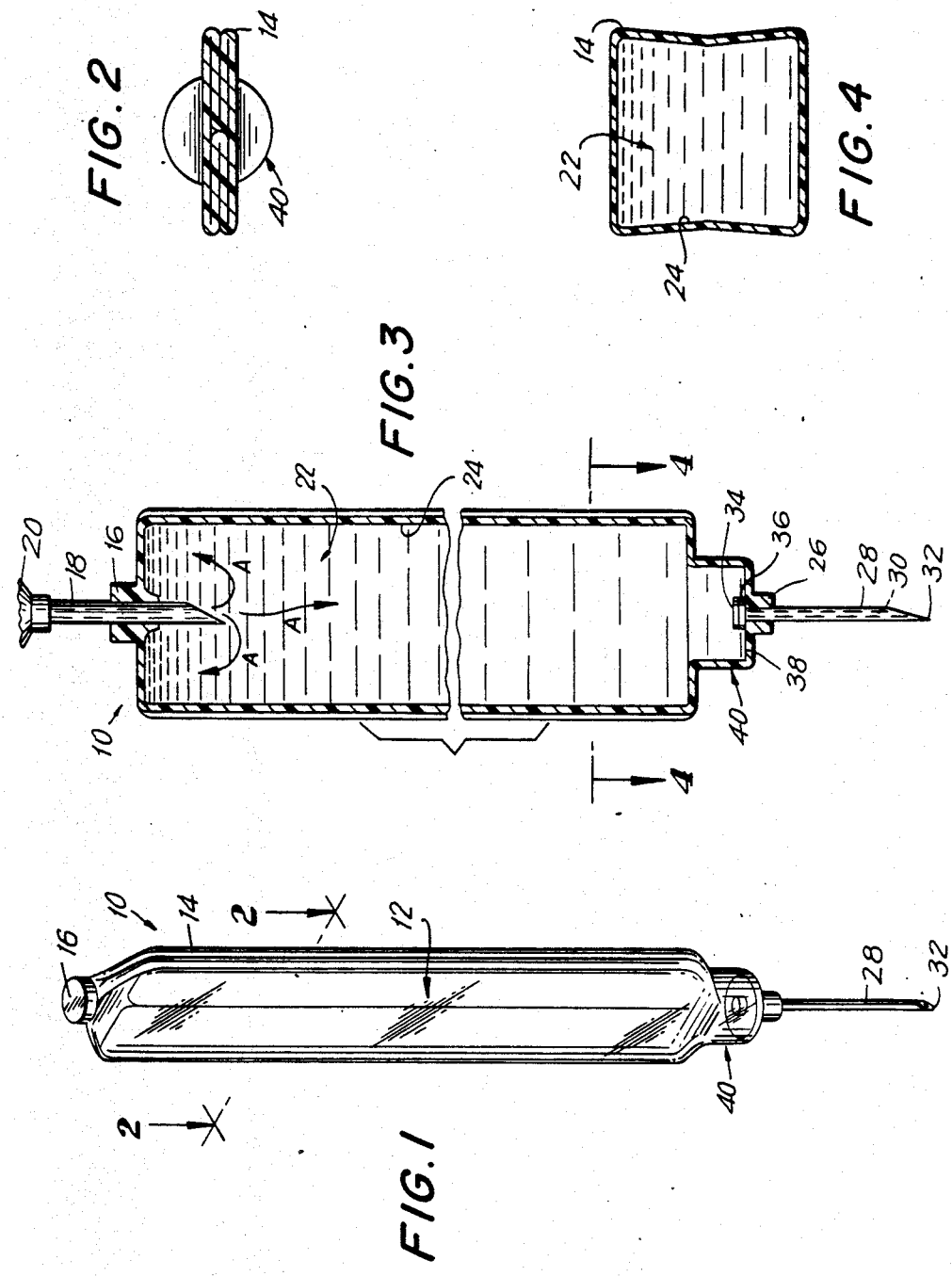

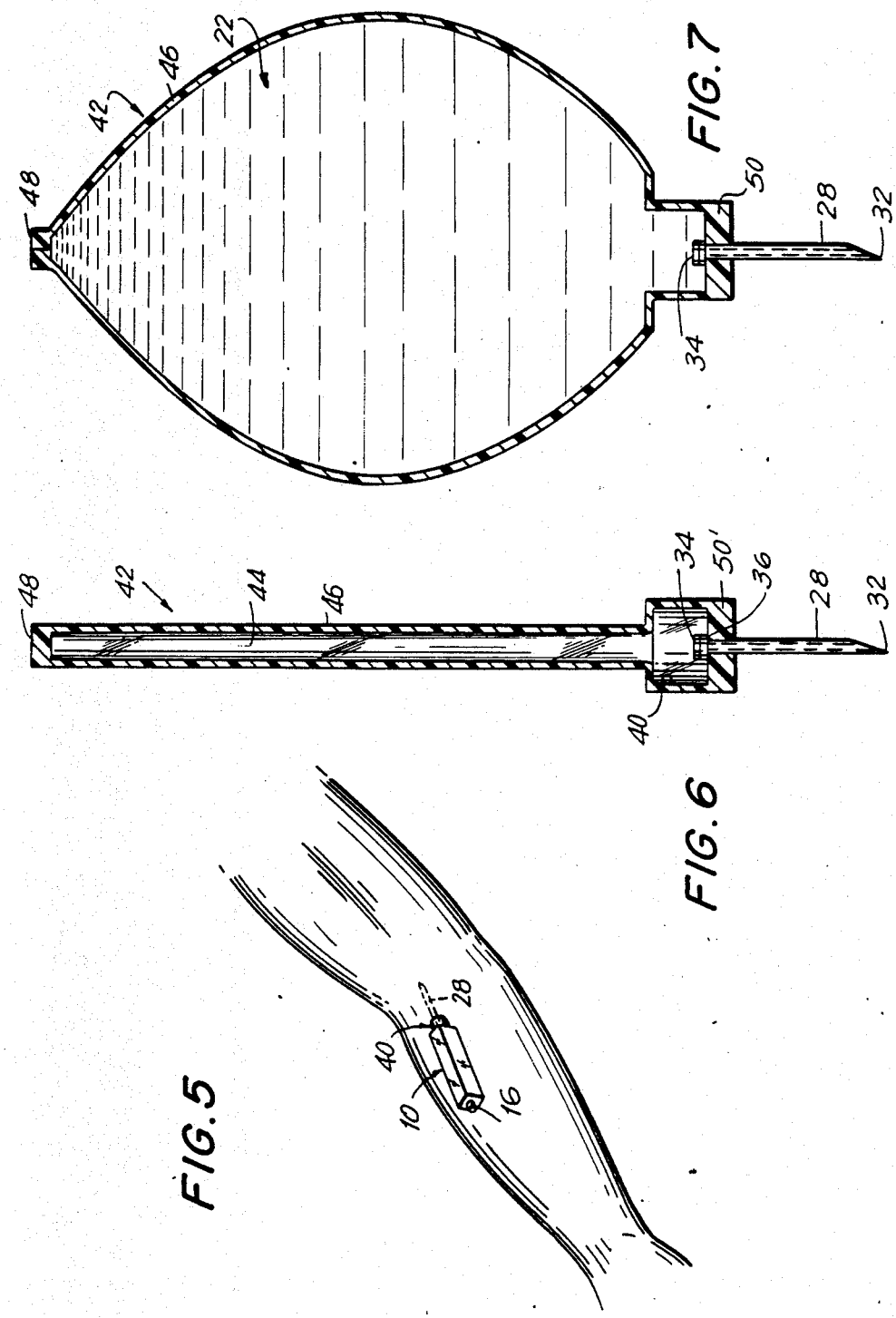

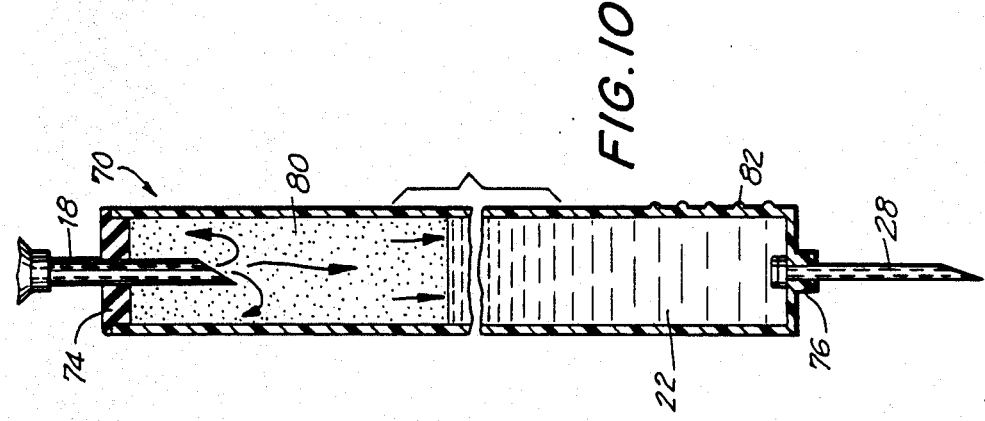
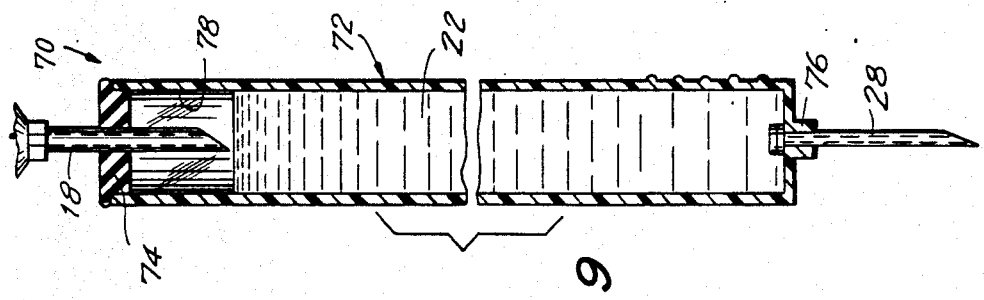
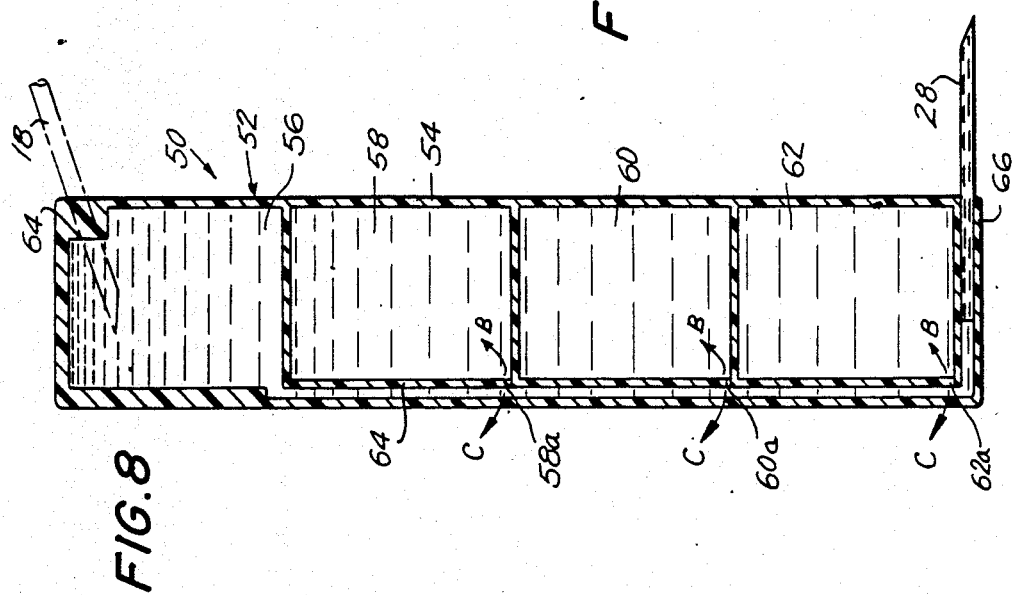

PARENTERAL FLUID MEDICATION RESERVOIR PUMP

BACKGROUND OF THE INVENTION

1. Field of the Invention

This invention generally relates to a pump for dispensing parenteral fluid medication and, more particularly, to a pump which continuously dispenses such medication in small doses over an extended period of time.

2. Description of the Prior Art

In-hospital dispensing arrangements for continuously dispensing fluid medication in small doses over extended periods of time to a patient are well known. Typically, such dispensing arrangements are of the gravity-feed intravenous type, and require large-sized bottles, long tubing, adjustable valves and, in general, a fairly elaborate set-up which is relatively expensive and unwieldy such that the set-up is not readily transportable from place to place. Power-driven medication pumps are also known, but these are much more expensive and even less readily transportable. An in-hospital patient hooked up to such a gravity-feed intravenous and/or power-driven pump arrangement cannot easily leave his or her bed and, even if the patient desires to be ambulatory, it certainly is a handicap for the patient to try to walk with such an elaborate set-up connected to the patient.

There are many situations where an out-patient has to receive medication, preferably on a continuous basis. For example, diabetics are typically injected with a periodic, e.g. daily, insulin dose at discrete times during the day. It would be more desirable if the diabetic would not receive the insulin in one or several massive doses, but, rather, if the insulin were administered in small doses over an extended time period. For this purpose, since the average diabetic cannot spend the day hooked up to a gravity-feed and/or power-driven pump dispensing arrangement, different types of delayed-action insulin have been prescribed. Nevertheless, rather than having the diabetic inject himself or herself with slow-acting and/or fast-acting insulin, it would be preferable if the diabetic could receive the insulin slowly and continuously without the economic and mobility restrictions imposed by known elaborate and expensive pump dispensing arrangements.

SUMMARY OF THE INVENTION

1. Objects of the Invention

It is a general object of this invention to overcome the aforementioned drawbacks of prior art medication dispensing arrangements.

It is another object of this invention to dispense fluid medication slowly, continuously, and in minute doses without restricting one's mobility or freedom to conduct his or her daily activities.

It is a further object of this invention to provide an inexpensive, yet highly accurate and reliable, fluid medication pump which is disposable after each use.

2. Features of the Invention

In keeping with these objects, and others which will become apparent hereinafter, one feature of this invention resides, briefly stated, in a parenteral fluid medication pump comprising a reservoir having an interior in which a parenteral fluid medication is contained, a tubular needle in fluid communication with the reservoir interior and having a pointed end insertable into a patient to be administered with the medication, and means for continuously discharging the medication along a flow path through the pointed end of the needle in small doses over an extended period of time.

In accordance with one embodiment of this invention, the discharging means includes elastic walls bounding the reservoir. The elastic walls are expandable from an original position upon the introduction of the fluid medication into the reservoir interior, to an expanded position in which the fluid medication exerts outward pressure on and expands the walls. The elastic walls are returnable from the expanded position at a slow rate of return toward the original position in which the returning elastic walls exert pressure on and force the fluid medication through the needle.

In accordance with another embodiment of this invention, the discharging means includes rigid walls bounding the reservoir, and means for filling a compressible gas under superatmospheric pressure into the reservoir interior. The gas is expandable to force the fluid medication through the needle.

Another advantageous feature of this invention is embodied in providing a membrane which is at least slightly permeable to the fluid medication. This membrane is mounted in the reservoir interior and in the flow path of the fluid medication upstream of the needle. A spacer means is advantageously employed for mounting the membrane above a base wall of the reservoir so that both sides of the membrane are wetted by the fluid medication.

The reservoir may have many configurations. A currently preferred shape for the reservoir is that the elastic walls are folded in a generally flattened, bellows-type shape in the original position, the elastic walls being distended to a generally rectangular shape in the extended position. Another desirable shape is to form the elastic walls slightly apart and parallel to each other in the original position, the elastic walls being distended in a generally outwardly-bulging balloon shape in the expanded position.

The novel features which are considered as characteristic of the invention are set forth in particular in the appended claims. The invention itself, however, both as to its construction and its method of operation, together with additional objects and advantages thereof, best will be understood from the following description of specific embodiments when read in connection with the accompanying drawings.

BRIEF DESCRIPTION OF THE DRAWINGS

FIG. 1 is a front perspective view of one embodiment of a pump in accordance with this invention prior to being filled with fluid medication;

FIG. 2 is a cross-sectional view taken along line 2—2 of FIG. 1;

FIG. 3 is a longitudinal sectional view of the FIG. 1 embodiment shown after being filled with a fluid medication;

FIG. 4 is a cross-sectional view taken along line 4—4 of FIG. 3;

FIG. 5 is a perspective view of the embodiment of FIGS. 1–4 on a reduced scale during use;

FIG. 6 is a longitudinal sectional view of another embodiment of a pump in accordance with this invention prior to being filled with fluid medication;

FIG. 7 is a view analogous to FIG. 6, but showing the pump after being filled with fluid medication;

FIG. 8 is a longitudinal sectional view of still another embodiment of a pump in accordance with this invention after being filled with fluid medication;

FIG. 9 is a longitudinal sectional view of yet another embodiment of a pump in accordance with this invention before being filled with a compressible gas; and FIG. 10 is a view of the pump of FIG. 9 after being filled with the compressible gas.

DETAILED DESCRIPTION OF THE PREFERRED EMBODIMENTS

Referring now to the drawings, reference numeral 10 generally identifies a first embodiment of a parenteral fluid medication pump having a reservoir 12 formed of elastic walls 14 which are expandable from an original position as shown, for example, in FIGS. 1 and 2, to an expanded position as shown, for example, in FIGS. 3, 4 and 5. The reservoir 12 has an inlet 16 through which a filling needle 18 of a partially-shown syringe 20 is inserted in order to introduce a quantity of a parenteral fluid medication 22 into the interior 24 of the reservoir 12. In the original position, the elastic walls 14 are folded in a generally flattened, bellows-type shape. Upon the introduction of the medication 22 in the direction of the arrows A, shown in FIG. 3, the medication exerts outward pressure on and expands the walls 14 until they assume the generally rectangular cross-sectional shape, as shown in FIG. 4. Once the reservoir 12 is filled with medication, the pump 10 is ready to dispense this medication to a patient.

For this purpose, the reservoir 12 is also provided with an outlet 26 through which a tubular needle 28, having an inner passage 30 extending along its length and a pointed end 32, is inserted into a patient to be administered with the fluid medication. For example, see FIG. 5 which shows the pump 10 in its expanded position, with the pointed end 32 of the needle positioned within a patient's arm. Although not shown, it will be understood that the pump 10 may be held in place on the patient's arm by various conventional fastening techniques, e.g., the pump may be taped on the arm, or a band may be tied about the arm and pump.

The interior passage 30 of the needle 28 is in fluid communication with the interior 24 of the reservoir and, in one preferred embodiment of this invention, the passage 30 has a cross-sectional area which is smaller than the cross-sectional area of the inner passage of a conventional needle. For example, if the cross-sectional area or diameter of an inner passage of a conventional needle, such as filling needle 18, is on the order of 20 mils, then the corresponding cross-sectional diameter of the inner passage 30 of the needle 28 is about 0.5 mils.

As pointed out earlier, the walls 14 are elastic, and are advantageously provided with a high memory characteristic so that the elastic walls 14 constantly seek to return from the expanded position to the original position. During the return of the elastic walls, the walls 14 exert pressure on and force the fluid medication 22 through the inner passage 30 and past the pointed end 32 into the patient. Due to the much smaller diameter of the inner passage 30, not all of the fluid medication can go through the needle 28 quickly and, in fact, due to the small cross-sectional diameter of the inner passage 30, the flow rate of the fluid medication out of the needle 28 is very slow. Indeed, in a preferred embodiment, the flow rate is on the order of one cu. cm. per eight hours.

It will be understood that the inner passage 30 of the needle represents the only avenue of escape for the fluid medication 22, since the inlet 16 is self-sealing once the filling needle 18 is removed. The inlet 16 is, in effect, a thickened solid wall which is pierced by the needle 18 prior to and during filling, but once the needle 18 is removed from the inlet 16 after filling, the pierced wall closes on itself due to the elastic nature of the materials constituting the inlet 16.

In order to provide a further measure of control over the flow rate of the medication, a semi-permeable membrane 34, e.g. a Teflon tradmark membrane, overlies the inner end of the needle 28. A mounting spacer 36 of annular shape, and preferably fabricated of cotton, is mounted between a bottom wall 38 of the reservoir 12 and the membrane 34 in order to wet both sides of the membrane 34. Depending on the osmotic characteristic of the membrane 34, it is possible that the needle 28 need not be provided with the very small diameter, e.g. on the order of 0.5 mils, for the passage 30, but, instead, a more conventionally-sized diameter on the order of 20 mils could be used.

Another feature of this invention resides in providing a compartment 40, preferably of rigid material, having a predetermined known interior volume. This compartment 40 is useful in calibrating the actual fluid medication flow. It can be expected that, because of tolerance variations in the manufacture of the reservoir 12 and/or the needle 28 and/or the membrane 34, as well as such variables as ambient temperature and the patient's body temperature, etc., the actual flow rate is different from the prescribed desired value. To monitor the actual flow rate for a particular set of circumstances, one can visually observe how long it takes for the known volume of medication within the compartment 40 to be discharged, and thereby control how much of the fluid medication should be introduced into the pump for dispensing purposes.

Another pump embodiment 42 is provided with a reservoir 44 formed with elastic walls 46 which are expandable from an original position, as shown in FIG. 6, to an outwardly-bulging expanded position, as shown in FIG. 7. The reservoir 44 has an inlet 48 through which a filling needle, as described previously, is inserted for filling purposes. The reservoir 44 has an outlet 50' at which are located the aforementioned discharge needle 28 having an inner passage 30 of miniature dimensions, and a pointed end 32, as well as the aforementioned membrane 34 and spacer 36. The reservoir 44 also has a calibration compartment 40 at its lower end.

The operation of the pump 42 is as described previously for pump 10, the only difference being that the elastic walls 46 are spaced slightly apart initially in mutual parallelism, as shown in FIG. 6, and are then outwardly bulged in an inflated balloon-like configuration, as shown in FIG. 7. As before, the miniature dimensions of the inner passage 30 of the needle 28 and/or the osmotic semi-permeable characteristic of the membrane 34 control the flow of fluid medication 22 to be continuous in small doses over an extended time period.

Another pump embodiment 50 shown in FIG. 8 has a reservoir 52 formed of elastic walls 54. In contrast to earlier embodiments, the reservoir 52 has multiple chambers 56, 58, 60, 62 in mutual fluid communication along a common conduit 63. Each chamber holds a proportionate share of the total amount of fluid to be dispensed. The reservoir 52 has an inlet 64 through which a filling needle 18, as previously described, is inserted for filling purposes. The reservoir 52 has an outlet 66 at which the aforementioned discharge needle 28 is located. The chambers 58, 60 and 62 have respective flap valves 58a, 60a, 62a, each valve being moved to open or close a respective chamber. Thus, during filling, the fluid medication first enters chamber 56, and then the pressure of the incoming medication pushes flap valves 58a, 60a, 62a, each in its turn, in the direction of arrows B to open the respective chamber, and allows the fluid medication to enter therein. Once the fluid pressure is equalized on both sides of each flap valve, the respective flap valves return to their initial positions in the direction of the arrows C until the respective chambers are sealed.

The operation of the pump 50 is essentially as described before, with the elastic walls of each chamber returning to their initial positions and exerting pressure on the fluid medication, and discharging the same through the needle 28. Once chamber 56 is emptied of medication, the pressure within chamber 58 becomes greater than the pressure in the common conduit 63 and, hence, the valve 58a is moved in the direction of the respective arrows C to open the chamber 58 and permit the fluid medication within the same to flow into the common conduit 63 for discharge through the needle 28. In turn, flap valves 60a and 62a are moved in the direction of their respective arrows C to open their respective chambers 60, 62 and permit the medication in the same to flow into the common conduit 63 for discharge through the needle 28. Hence, each chamber, in its turn, is emptied of its medication. The successive collapse of each chamber can be tactilely felt by the patient in order to monitor the progress of the dispensing operation.

Still another embodiment is shown in FIGS. 9 and 10 wherein a pump 70 comprises a reservoir 72 formed of rigid walls. The rigid reservoir 72 has an inlet 74 through which a filling needle 18, as described previously, is inserted for filling purposes. The reservoir 72 also has an outlet 76 at which the aforementioned discharge needle 28 is located.

In contrast to previous embodiments, the fluid medication 22 does not entirely fill the interior of the reservoir 72. Instead, as best shown in FIG. 9, a space 78 is formed between the upper level of the fluid medication and the inlet 74 within the reservoir. A filling needle, either the same and/or a different needle as compared to the previously described filling needle 18, is used to introduce a compressible gas 80 into the space 78. The volume of gas introduced is greater than the volume of the space 78 so that the gas 80 is compressed and constantly seeks to expand. During this gaseous expansion, the expanding gas exerts a constant force on the medication and continuously discharges the same in small doses over an extended time. Hence, the expanding gas serves as the functional equivalent of the aforementioned returning elastic walls of the reservoir. The inlet 74 self-closes once the filling needle 18 is removed therefrom, thus ensuring that the needle 28 serves as the only avenue of escape for the medication 22.

As also shown in FIGS. 9 and 10, indicator means or ridges 82 are provided at the exterior of the pump 70 in order to provide a visual indication for the patient to monitor the flow rate of the medication from the pump. These ridges can be consulted throughout the dispensing operation.

It will be understood that each of the elements described above, or two or more together, also may find a useful application in other types of constructions differing from the types described above.

While the invention has been illustrated and described as embodied in a parenteral fluid medication reservoir pump, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

1. A disposable parenteral fluid medication pump, comprising:
   (a) an elongated reservoir expandable to an expanded position and collapsible to an original position, said reservoir having a pair of end walls spaced longitudinally apart of each other by a constant longitudinal distance, a pair of generally planar side walls integral with and extending longitudinally between the end walls, said side walls lying in parallel planes and being movable toward and away from each other in mutual parallelism in a transverse direction generally perpendicular to their planes to bound a variable transverse distance, and a pair of elastic walls integral with and extending between the side walls, said elastic walls being foldable toward and away from each other, all of said walls bounding an interior;
   (b) a closeable inlet at one end wall and through which a parenteral fluid medication is introduced into the interior of the reservoir to expand the reservoir due to outward pressure exerted by the medication to the expanded position in which the side walls are moved far apart of each other and the elastic walls are unfolded to form a generally rectangular cross-section for the reservoir;
   (c) a needle mounted at and extending through the other end wall, said needle being in fluid communication with the interior of the reservoir and having a pointed end insertable into a patient to be administered with the medication; and
   (d) said elastic walls having a memery characteristic with a slow rate of return and being foldable toward each other, while concomitantly linearly and transversely moving the side walls closer together, from the expanded position to the original position during which the linearly moving side walls controllably and continuously discharge the medication through the pointed end of the needle in small doses over an extended period of time.

2. The pump as recited in claim 1, and further comprising an asmatic membrane which is at least slightly permeable to the fluid medication, said membrane being mounted in the reservoir interior and in the flow path of the fluid medication upstream of the needle.

3. The pump as recited in claim 2, wherein the reservoir has a base wall; and further comprising spacer means for mounting the membrane above the base wall so that both sides of the membrane are wetted by the fluid medication.

4. The pump as recited in claim 1, wherein the reservoir includes a rigid walled calibration compartment having a predetermined known interior volume.

* * * * *